United States Patent
Rockstroh et al.

(10) Patent No.: US 10,422,058 B2
(45) Date of Patent: Sep. 24, 2019

(54) KNITTED-FABRIC PART FOR ORTHOPEDIC AND PROSTHETIC DEVICES

(71) Applicant: Ossur Iceland ehf, Reykjavik (IS)

(72) Inventors: Martin Rockstroh, Creussen (DE); Cornelia Kausler, Schlammersdorf (DE); Nikolai Witt, Bindlach (DE)

(73) Assignee: OSSUR ICELAND EHF, Reykjavik (IS)

(*) Notice: Subject to any disclaimer, the term of this patent is extended or adjusted under 35 U.S.C. 154(b) by 122 days.

(21) Appl. No.: 15/449,280

(22) Filed: Mar. 3, 2017

(65) Prior Publication Data

US 2017/0254004 A1 Sep. 7, 2017

(30) Foreign Application Priority Data

Mar. 4, 2016 (DE) .................. 10 2016 103 960

(51) Int. Cl.
*D04B 1/26* (2006.01)
*D04B 13/00* (2006.01)
*A61F 2/78* (2006.01)
*A61F 5/01* (2006.01)
*D04B 1/18* (2006.01)
*D04B 1/24* (2006.01)
*D04B 19/00* (2006.01)
*D04B 1/10* (2006.01)

(52) U.S. Cl.
CPC ............ *D04B 13/00* (2013.01); *A61F 2/7812* (2013.01); *A61F 5/0102* (2013.01); *D04B 1/106* (2013.01); *D04B 1/18* (2013.01); *D04B 1/24* (2013.01); *D04B 1/26* (2013.01); *D04B 19/00* (2013.01); *A61F 2002/7818* (2013.01); *A61F 2002/7837* (2013.01)

(58) Field of Classification Search
CPC . D04B 1/26; D04B 1/265; D04B 9/46; D04B 9/52
See application file for complete search history.

(56) References Cited

U.S. PATENT DOCUMENTS 366,105 A * 7/1887 Hoyroyd .................. D04B 9/54
66/172 R
663,749 A 12/1900 Gorse
(Continued)

FOREIGN PATENT DOCUMENTS

DE 640471 C 1/1937
DE 658921 C 4/1938
(Continued)

OTHER PUBLICATIONS

International Search Report From PCT Application No. PCT/US2017/020692, dated May 26, 2017.
(Continued)

*Primary Examiner* — Danny Worrell
(74) *Attorney, Agent, or Firm* — Workman Nydegger

(57) ABSTRACT

A knitted-fabric part including a basic part knitted with at least one knitted-fabric thread, and at least one extension part attached to the basic part to form a contiguous and intact structure. At least one unravelable connecting thread attaches the basic part to the at least one extension part, such that removal of the at least one unravelable connecting thread separates the basic part from the at least one extension part.

20 Claims, 3 Drawing Sheets

(56) References Cited

U.S. PATENT DOCUMENTS

| | | | |
|---|---|---|---|
| 940,585 A | 11/1909 | Drennan | |
| 967,585 A | 8/1910 | Teufel | |
| 1,544,641 A | 7/1925 | Guinzburg | |
| 1,890,299 A | 12/1932 | Mutchler et al. | |
| 2,113,763 A * | 4/1938 | Leimbrock | D04B 1/22 66/1 R |
| 2,169,203 A | 8/1939 | Hinchliff | |
| 2,255,224 A | 9/1941 | Luhn | |
| 2,268,751 A | 1/1942 | Harris | |
| 2,420,960 A | 5/1947 | Larkin | |
| 2,494,927 A * | 1/1950 | Burd | A41B 11/12 2/239 |
| 2,669,726 A * | 2/1954 | Meisel | A41F 9/02 2/221 |
| 2,724,120 A * | 11/1955 | Biern | A41D 15/002 2/211 |
| 2,881,603 A * | 4/1959 | Vendetti | D04B 9/24 66/172 R |
| 3,099,266 A | 7/1963 | Spitzer | |
| 3,451,232 A | 6/1969 | Belzidsky | |
| 3,789,842 A | 2/1974 | Froimson | |
| 3,845,506 A * | 11/1974 | Harris | A41B 11/14 2/240 |
| 4,027,667 A | 6/1977 | Swallow et al. | |
| 4,172,456 A | 10/1979 | Zens | |
| 4,176,665 A | 12/1979 | Terpening | |
| 4,201,203 A | 5/1980 | Applegate | |
| 4,237,707 A | 12/1980 | Safrit et al. | |
| 4,379,463 A | 4/1983 | Meier et al. | |
| 4,479,272 A | 10/1984 | Beldzisky | |
| 4,492,227 A | 1/1985 | Senn et al. | |
| 4,632,106 A | 12/1986 | Gamm | |
| 4,822,371 A | 4/1989 | Jolly et al. | |
| 4,870,956 A | 10/1989 | Fatool et al. | |
| 4,908,037 A | 3/1990 | Ross | |
| 4,923,474 A | 5/1990 | Klasson et al. | |
| 5,007,418 A | 4/1991 | Bartizal et al. | |
| 5,036,837 A | 8/1991 | Mitchell et al. | |
| 5,115,650 A | 5/1992 | Patrick et al. | |
| 5,133,199 A | 7/1992 | Parikh et al. | |
| 5,139,477 A | 8/1992 | Peters | |
| 5,263,923 A | 11/1993 | Fujimoto | |
| 5,277,697 A | 1/1994 | France et al. | |
| 5,334,135 A | 8/1994 | Grim et al. | |
| 5,367,708 A | 11/1994 | Fujimoto | |
| 5,382,223 A | 1/1995 | Springs | |
| 5,385,538 A | 1/1995 | Mann | |
| 5,407,421 A | 4/1995 | Goldsmith | |
| 5,419,161 A | 5/1995 | Bodenschatz et al. | |
| 5,474,524 A | 12/1995 | Carey | |
| 5,507,834 A | 4/1996 | Laghi | |
| 5,538,488 A | 7/1996 | Villepigue | |
| 5,588,956 A | 12/1996 | Billotti | |
| 5,593,454 A | 1/1997 | Helmy | |
| 5,640,714 A | 6/1997 | Tanaka | |
| 5,695,452 A | 12/1997 | Grim et al. | |
| 5,728,057 A | 3/1998 | Ouellette et al. | |
| 5,729,836 A * | 3/1998 | Ewing | A41B 11/003 2/409 |
| 5,730,710 A | 3/1998 | Eichhorn et al. | |
| 5,769,809 A | 6/1998 | Witzel | |
| 5,830,237 A | 11/1998 | Kania | |
| 5,865,776 A | 2/1999 | Springs | |
| 5,897,517 A | 4/1999 | Laghi | |
| 6,055,673 A * | 5/2000 | McCormick | A41D 1/06 2/227 |
| 6,059,834 A | 5/2000 | Springs | |
| 6,092,397 A | 7/2000 | Cortinovis | |
| 6,136,039 A | 10/2000 | Kristinsson et al. | |
| 6,139,929 A | 10/2000 | Hayton et al. | |
| 6,149,616 A | 11/2000 | Szlema et al. | |
| 6,149,690 A | 11/2000 | Belzidsky | |
| 6,282,729 B1 | 9/2001 | Oikawa et al. | |
| 6,308,538 B1 * | 10/2001 | Wood | D04B 1/22 66/169 R |
| 6,401,498 B1 * | 6/2002 | Fujiwara | A41D 27/10 2/243.1 |
| 6,485,776 B2 | 11/2002 | Janusson et al. | |
| 6,572,574 B2 | 6/2003 | Gardon-Mollard | |
| 6,592,539 B1 | 7/2003 | Einarsson et al. | |
| 6,634,190 B2 | 10/2003 | Didier-Laurent | |
| 6,706,364 B2 | 3/2004 | Janusson et al. | |
| 6,726,641 B2 | 4/2004 | Chiang et al. | |
| 6,823,700 B1 * | 11/2004 | Yi | D04B 21/02 66/192 |
| 6,964,688 B1 | 11/2005 | Kania | |
| 7,025,738 B2 | 4/2006 | Hall | |
| 7,083,586 B2 | 8/2006 | Simmons et al. | |
| 7,090,651 B2 | 8/2006 | Chiang et al. | |
| 7,118,602 B2 | 10/2006 | Bjarnason | |
| 7,169,189 B2 | 1/2007 | Bjarnason et al. | |
| 7,273,464 B2 | 9/2007 | Reinhardt | |
| 7,297,128 B2 | 11/2007 | Binder et al. | |
| D574,084 S | 7/2008 | Reinhardt | |
| 7,418,837 B2 * | 9/2008 | Muller | D04B 21/20 66/170 |
| 7,473,236 B1 | 1/2009 | Mathewson | |
| 7,517,331 B2 | 4/2009 | Reinhardt et al. | |
| 7,625,350 B2 | 12/2009 | Hunter et al. | |
| 7,713,222 B2 | 5/2010 | Evans et al. | |
| 7,749,181 B2 | 7/2010 | Simmons et al. | |
| 7,819,830 B2 | 10/2010 | Sindel et al. | |
| 7,959,590 B2 | 6/2011 | Scott | |
| 8,025,632 B2 | 9/2011 | Einarsson | |
| 8,034,120 B2 | 10/2011 | Egilsson et al. | |
| 8,043,242 B2 | 10/2011 | McSpadden et al. | |
| 8,048,014 B2 | 11/2011 | Brown | |
| 8,066,654 B2 | 11/2011 | Sandifer et al. | |
| 8,118,765 B2 | 2/2012 | Magnusson | |
| 8,123,818 B2 | 2/2012 | Bjarnason et al. | |
| 8,286,268 B2 * | 10/2012 | Yamashita | A41D 15/002 2/269 |
| 8,328,747 B2 | 12/2012 | Matsunaga | |
| 8,904,829 B2 * | 12/2014 | Keitch | D04B 21/16 66/195 |
| 9,393,147 B2 | 7/2016 | Scheuermann et al. | |
| 9,506,172 B2 | 11/2016 | Atmanspacher | |
| 2002/0183859 A1 | 12/2002 | Houser | |
| 2005/0020951 A1 | 1/2005 | Gaylord et al. | |
| 2005/0101693 A1 | 5/2005 | Arbogast et al. | |
| 2007/0033711 A1 | 2/2007 | Achtelstetter | |
| 2007/0043450 A1 | 2/2007 | Pickering et al. | |
| 2007/0060853 A1 | 3/2007 | Sindel et al. | |
| 2009/0156973 A1 | 6/2009 | Scott | |
| 2010/0036303 A1 | 2/2010 | Bauerfeind et al. | |
| 2010/0274363 A1 | 10/2010 | Laghi et al. | |
| 2011/0098827 A1 | 4/2011 | Laghi et al. | |
| 2011/0208321 A1 | 8/2011 | Doddroe et al. | |
| 2011/0270414 A1 | 11/2011 | Laghi et al. | |
| 2012/0277649 A1 | 11/2012 | Matsuo et al. | |
| 2013/0110023 A1 | 5/2013 | Scheuermann et al. | |
| 2014/0276300 A1 | 9/2014 | Reinhardt et al. | |
| 2014/0303534 A1 | 10/2014 | Huffa et al. | |
| 2014/0316312 A1 | 10/2014 | Atmanspacher | |
| 2015/0057763 A1 | 2/2015 | Halldorsson et al. | |

FOREIGN PATENT DOCUMENTS

| | | |
|---|---|---|
| DE | 682936 C | 10/1939 |
| DE | 1635951 A1 | 7/1971 |
| DE | 9417913 U1 | 3/1995 |
| DE | 102011118617 A1 | 5/2013 |
| DE | 102013103914 B3 | 3/2014 |
| DE | 102013010371 B4 | 2/2015 |
| EP | 0498062 A1 | 8/1992 |
| EP | 0835645 A1 | 4/1998 |
| EP | 2283795 A1 | 2/2011 |
| EP | 2526791 A1 | 11/2012 |
| EP | 2815728 A1 | 12/2014 |

(56) References Cited

FOREIGN PATENT DOCUMENTS

| FR | 2807644 A1 | 10/2001 |
|----|------------|---------|
| WO | 2009003486 A1 | 1/2009 |
| WO | 2012003992 A1 | 1/2012 |

OTHER PUBLICATIONS

Rosner, "In Praise of Seams", Twist Collective, http://www.twistcollective.com/articlepdfs/seaming.pdf, 2011, 9 Pages.

Otto Bock Healthcare LP, Prosthetics—Lower Extremities, "Knee and Thigh Sleeves", retrieved from www.ottobockus.com, 1 page, Jul. 1, 2014.

International Search Report and Written Opinion of the International Searching Authority from International Application No. PCT/US2014/051445, dated Nov. 21, 2014.

Product Information, "BORT AsymmetricPlus, No. 114900, Unit PCE", Downloaded Mar. 31, 2014, 3 Pages. Retrieved at http://shop.bort.de/en/produkt-details.aspx?ProductNo=114900.

Product Information, "BORT AsymmetricPlus, No. 114700, Unit PCE", Downloaded Mar. 31, 2014, 3 Pages. Retrieved at http://shop.bort.de/en/produkt-details.aspx?ProductNo=114700.

Brochure, "BORT Asymmetric Plus, Die Mehrwert-Orthese bei Patella-Luxation", Downloaded Aug. 2012. 16 Pages. Retrieved at http://bort.com.

International Search Report from PCT Application No. PCT/US2014/033265, dated Jul. 10, 2014.

German Search Report from DE Application No. 102016103960.8, dated Nov. 21, 2016.

\* cited by examiner

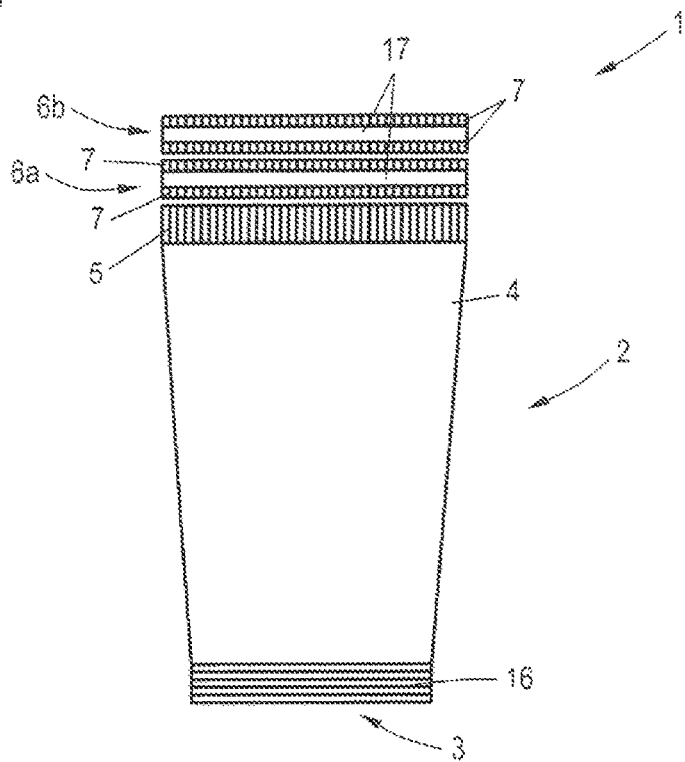
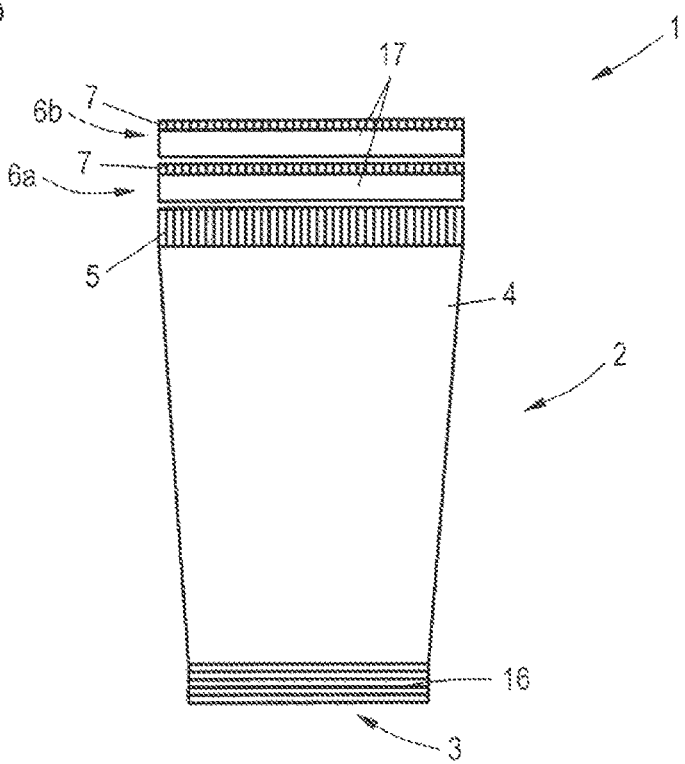

KNITTED-FABRIC PART FOR ORTHOPEDIC AND PROSTHETIC DEVICES

FIELD OF THE DISCLOSURE

The disclosure relates to a knitted-fabric part in the form of a sock or sleeve, and having a basic part knitted with at least one unravelable thread connecting to at least one extension part.

BACKGROUND

In the field of orthopedic and prosthetic devices, a knitted-fabric part in the form of a leg sock or sleeve may be used as a volume compensation sock or sleeve in connection with a prosthetic leg. When used as a sock, the knitted-fabric part is drawn directly on the residual limb. As for a volume compensation sock, the knitted-fabric part is drawn over a suspension liner disposed on a residual limb, to allow volume variations and a dimension difference between the residual limb and a prosthesis. When used as a sleeve, the knitted-fabric part is drawn over a limb to protect the arm or to cover irritated parts of the skin.

Prosthetic suspension liners or sleeves have been described in prior patents, such as U.S. Pat. No. 4,923,474, issued May 8, 1990; U.S. Pat. No. 6,136,039, issued Oct. 24, 2000; U.S. Pat. No. 6,485,776, issued Nov. 26, 2002; U.S. Pat. No. 7,118,602, issued Oct. 10, 2006; and U.S. Pat. No. 7,169,189, issued on Jan. 30, 2007, each of which are incorporated herein by reference. These liners or sleeves may be fabricated of elastic or elasticized materials, and are used to cushion a post-operative stump or residual limb regarding a prosthesis, such as a socket, that is installed over the residual limb and coupled to the liner or sleeve by a conventional locking element.

User anatomies have different dimensions and a clinic must account for these dimensions by stocking knitted-fabric parts in different sizes. This requires a large inventory of parts that can be readily available for a user. To address this issue, it is known to shorten and adapt the knitted-fabric part by cutting off a length portion. Reducing the length of a knitted-fabric part by cutting has the drawback in that the cut edge of the knitted-fabric part must be subsequently sewn since it is frayed along the cut edge, so the newly sized knitted-fabric part does not unravel during use.

SUMMARY

Embodiments of the disclosure include a knitted-fabric part arranged with a first separable extension part with an unravelable connecting thread. The knitted-fabric part may comprise at least two segments, namely a basic part formed from a knitted fabric, which forms a first segment, and an extension part formed from a knitted fabric, which forms the second segment. The two segments are interconnected by at least the unravelable connecting thread, and are contiguous to form an intact, elongate knitted-fabric part.

If the knitted-fabric part is too long and must be adapted to a user's specific anatomy, the length of the knitted-fabric part may be reduced by unravelling the connecting thread between the first and second segments. Unravelling the connecting thread leads to a separation of the extension part from the basic part. The knitted-fabric part is shortened by the length of the removed extension part, and only the basic part remains as the sock or sleeve.

From the foregoing, a simple shortening of the knitted-fabric part length and an adaptation to an accordingly short limb or an accordingly short residual limb is possible. The expense of cutting off segments of a sock or sleeve, and the requirement to sew the remaining parts are eliminated. The hassle of stocking many sized socks and sleeves is likewise eliminated by the embodiment of the knitted-fabric part.

According to an embodiment, the knitted-fabric part has two segments comprising the basic part and at least one extension part separable yet attached to the basic part. The at least one extension part may comprise multiple extension parts extending in a longitudinal direction of the knitted-fabric part and from the basic part. The at least one extension part includes first and second adjacent extension parts respectively interconnected through an unravelable connecting thread. In this embodiment, several extension parts are connected one after the other, i.e. cascaded, so the entire knitted-fabric part comprises over two extension parts, and the basic parts. Like the basic part and the first extension part, the additional extension parts following the first extension part are interconnected through discrete, additional connecting threads.

The arrangement makes it possible for a long knitted-fabric part to be shortened to various lengths. If the knitted-fabric part comprises five extension parts, it is possible to realize, starting out from the original length, five further knitted-fabric part lengths, by either the extension part at the edge side being separated, or the two extension parts at the edge side. There is a high adaptability of the knitted-fabric part to the actual length of the user's anatomy.

To avoid a curling of the basic part or the respective extension part, if it forms the edge of the knitted-fabric part, after the separation of the extension part placed ahead, the basic part is terminated at the end facing the first extension part through a knitted cuff with a definitive firm edge, and the first extension part and each further extension part is knitted as a cuff with definitive firm edge on both sides or has a cuff with a definitive firm edge also on the side which faces away from the extension part which respectively lies closer to the basic part. By the meaning of a definitive firm edge, it is intended that the edge is devoid of fraying, and it is complete in the sense it does not require further modification. The firm edge is intact, and discrete.

The basic part is provided with a cuff at the edge at which the first extension part is fixed through the connecting thread. Such a cuff is usually knitted with net course and a following knitting structure ("structure") of 1:1 or right/right or a tubular structure. It cannot curl because of this structure type. If the first extension part is separated, the basic part forms the remaining knitted-fabric part, the non-curling cuff forms the edge of the knitted-fabric part. Such a cuff is elastic because of the respective structure type and fixes the knitted fabric to the leg or arm. Beyond the cuff region, the basic part may be knitted with an arbitrary structure type, e.g. with one of the above-mentioned structures or a right/left structure or left/left structure. It will be remembered that this list is not exhaustive.

To prevent all the extension parts, when forming the edge of the knitted-fabric part, from curling or unravelling, the respective extension part may either be knitted over its entire length as a cuff or knitted as a cuff with a definitive firm edge on one or both sides, i.e. in 1:1 structure or right/right structure or tubular structure. Curling or unravelling is eliminated in such arrangements. The respective extension part may be knitted in a different knitted-fabric type over a part of its length, at the side facing away from the basic knitted-fabric of the respective extension part with a knitted cuff having a firm edge. Each extension part may have a corresponding, non-curling cuff, if it forms the edge of the knitted-fabric part. This configuration of the knitted-fabric part ensures that independent of the "plane" in which the knitted-fabric part is shortened, a cuff forms the edge or the terminal end of the knitted-fabric part, which can neither curl nor unravel. For the connection of an extension part with another extension part or with the basic part, no cuff is preferably provided at the side of the extension part, which lies closer to the basic part. It is merely necessary to knit in the connecting thread at this edge. In a variation, however, the edge of the respective extension part which lies closest to the basic part may have a cuff provided with a firm edge. Here, an extension part may have on its edge a cuff, which extends over a lower or higher number of stitch courses between two cuffs, rather than being knitted from an arbitrary basic knitted fabric.

As described, the coupling of the basic part and first extension part or extension parts among each other is effected through respectively one discrete connecting thread. This can be knitted either right/left, right/right, or in a tubular structure. All these types of knitted fabric allow the parts of the knitted-fabric part to be connected to each other. They can be firmly tied to each other through the connecting thread, so the knitted-fabric part can be drawn over the residual limb, the leg, or the arm also by strongly drawing it. However, an unravelling of the connecting thread knitted with these types of structures is readily possible. In a preferred variation, a right/left structure is preferred, because a connecting thread knitted in this way can relatively simply be drawn out from its respective structure with the basic knitted fabric or with the extension part. In this structure type, there are fewer points of contact in the stitches of the interconnected parts, so that less friction is given upon drawing and the connecting thread is easier to unravel. For drawing out the connecting thread, the protruding end of the connecting thread at the inner side may be detached, and the connecting thread may be cut open at the opposing side. The thread can be drawn out in two halves.

For facilitating the discovering of the connecting thread, the one or each connecting thread is preferably configured in a color different from that of the thread of the basic knitted-fabric. The connecting thread is optically identifiable and accordingly can be cut open or drawn out. A color difference, however, is not compulsory, and not when respectively two cuffs are interconnected through the connecting thread. Because upon drawing the knitted-fabric part in the longitudinal direction of the knitted fabric the connecting thread will be readily recognizable between the two cuffs and can be cut and drawn accordingly.

To allow a tubular knitted-fabric part to be drawn over a residual limb, a leg, or an arm, the knitted-fabric part may be open at the side at which the one or more extension parts are provided. At the opposing side it can be open, but it can also be closed. If the knitted-fabric part is configured as a stump sock, it is preferably closed, so it covers the stump also at the underside of the stump. With a volume compensation sock it must be open at the lower end, so the liner can protrude therefrom. If it is a simple leg sock, the end can be open, that is, that no foot part is provided. It is also conceivable here to knit a foot part to the lower end.

The knitted-fabric part itself can be configured as a flat knitted fabric or circular knitted fabric. This applies to the basic part and to each extension part. If they are configured as a flat knitted fabric, they may have a longitudinal seam; such a longitudinal seam will not be present with a circular knitted fabric.

The knitted-fabric part itself has either a cylindrical or a conical basic form, i.e. a tubular basic form. If it is designed as a volume compensation sock, a cylindrical basic form can be provided. If it is provided as a longer leg sock or as a longer arm sock, a conical basic form may be expedient.

As already described, the knitted-fabric part, when configured as a leg sock, can be configured as a volume compensation sock for the usage of a liner to be drawn over a leg sock. Such a system is known for example from EP 2815728 B1. It can also be a stump sock. If the knitted-fabric part is configured as a volume compensation sock, this has an adhesive layer preferably near its distal end at the inner side of the knitted fabric. The adhesive layer cooperates adhesively with the surface of the described liner and prevents the volume compensation sock from being pushed upward upon getting into the prosthesis shaft, i.e. slipping off the liner surface. The adhesive layer can be sewed or glued in the form of an adhesive band, it can also be poured, spread or melted onto the knitted fabric and be cured or cross-linked. Here the adhesive layer is applied by means of an initially fluid material, which can be effected by pouring and spreading, thereafter the adhesive layer cures or cross-links by heating with UV or IR irradiation or the like. It can also be applied by melting it or subsequent curing or cross-linking.

When melting or subsequently curing or cross-linking, first an adhesive band is placed which then is melted by heating, for example by high-frequency heating or ultrasound heating, direct heating using heatable plates or the like, so it wets the knitted fabric (as in the spreading or pouring solution) and a bond or an appropriate permeating into the knitted fabric is the result. Thereafter, the curing or cross-linking is effected so that the adhesive layer is securely fixed to the knitted fabric. As an adhesive material is preferably used a stretchable elastomer or an elastomer gel which may include an elastomer and a plasticizer oil and cross-links sufficiently, whereby in particular the use of a styrenic block copolymer, whether as a pure polymer or as a gel component, has turned out to be expedient regarding an adhesive bond in particular to the silicone/polyurethane surface or sliding layer surface of a liner. Preferably, the elastomer styrene ethylene propylene styrene (SEPS) is used.

The basic part and the one or more extension parts are preferably knitted from at least one knitted-fabric thread. This may be a thread made of PA, PP, PES or a natural thread made of cotton or silk. Also, two or more of such knitted-fabric threads can be knitted in parallel. Regarding the thread material of the connecting thread, the same thread types can be used. An elastic thread may be knitted into the fabric or is led as a weft thread through the stitches to impart an elastic or compressive property to the knitted-fabric part.

These and other features, aspects, and advantages of the present disclosure will become better understood regarding the following description, appended claims, and accompanying drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of a prosthetic or orthopedic device, and in no way limit the structures or configurations according to the present disclosure.

FIG. 4 is a schematic diagram of a knitted-fabric part of a third embodiment with two extension parts with a cuff provided on both sides thereof.

FIG. 5 is a schematic diagram of a knitted-fabric part of a fourth embodiment with two extension parts with cuff provided on only one side thereon.

DETAILED DESCRIPTION OF VARIOUS EMBODIMENTS

Figure 1:
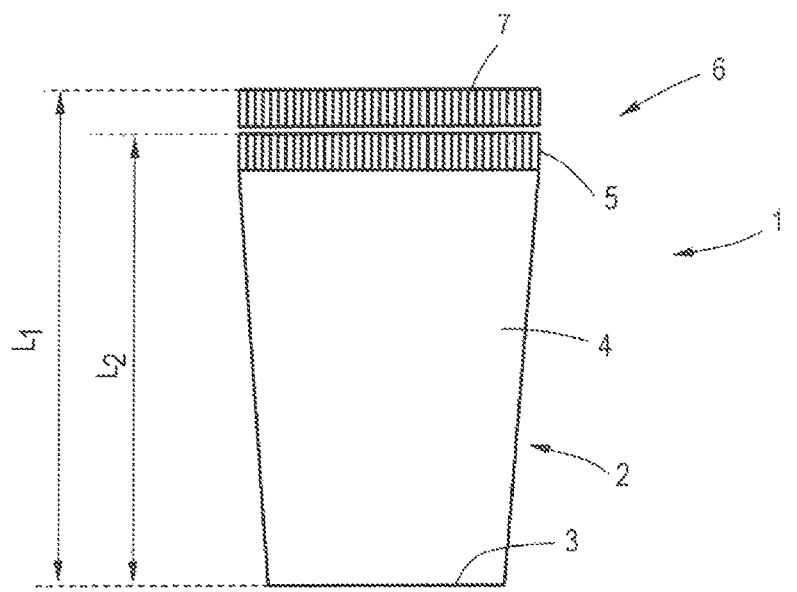
FIG. 1 is a schematic diagram of a knitted-fabric part according to the disclosure of a first embodiment including a basic part and at least one extension part.

FIG. 1 shows in a schematic diagram a knitted-fabric part 1 according to the disclosure in a first embodiment. It is configured as a tubular leg sock or sleeve, and can be knitted as a flat or circular knitted-fabric part.

The knitted-fabric part 1 includes a basic part 2 forming the essential or base part of the knitted-fabric part that is preferably not reduced in length, which is knitted with at least one knitted-fabric thread from PA or PP. The basic part 2 preferably has a cylindrical or tubular, slightly conical basic form and in the shown example is configured in a closed fashion near its lower end 3. It may be a leg sock with closed lower end.

The basic part 2 has two portions, namely the essential basic part portion 4 defining nearly the total length, in which an arbitrary basic part structure is knitted. Further, near the upper end of the basic part 2, adjoining the basic part portion 4, there is knitted a cuff 5 with a firm edge, through which cuff 5 the basic part is terminated at the upper end. The cuff 5, which is knitted from the same knitted-fabric thread as the basic knitted-fabric portion 4, is knitted with a usual right/right structure or 1:1 structure.

To the basic part 2 or to the cuff 5 there is tied, through an unravelable connecting thread, in the shown example, an extension part 6, which is also annular, tubular or cylindrical, and elongates the basic part 2. In the shown example, it is also knitted as a cuff 7, but with firm edge on both sides. The length of the extension parts 6 knitted as a cuff 7 may correspond to the length of the cuff 5 of the basic part 2, but this need not be the case. Rather, the extension part 6 can also be longer or shorter than the cuff 5 of the basic knitted-fabric part 2. In the shown embodiment example, one extension part 6 forms the upper end of the knitted-fabric part 1. As it is knitted as a cuff 5, as described, the knitted-fabric part 1 is prevented from curling near its upper end.

As shown in FIG. 1, the knitted-fabric part 1 has a total length $L_1$ defined by the length of the basic part 2 and the length of the extension part 6. If this knitted-fabric part 1 is too long to be worn for the user, the user can now by simply unravelling and drawing out the separating thread (not shown) reduce the length of the knitted-fabric part 1 by the length of the extension part 6. When the separating thread is detached, the extension part 6 can be separated, so the remaining knitted-fabric part 1 merely has the length $L_2$. The length may correspond to the length of the basic part 2 in the shown embodiment example. As the basic part 2 with separated extension part 6 is likewise terminated with a cuff 5, with a shortened knitted-fabric part 1, it is ensured that the upper end of the shortened knitted-fabric part 1 cannot curl or unravel.

Figure 2:
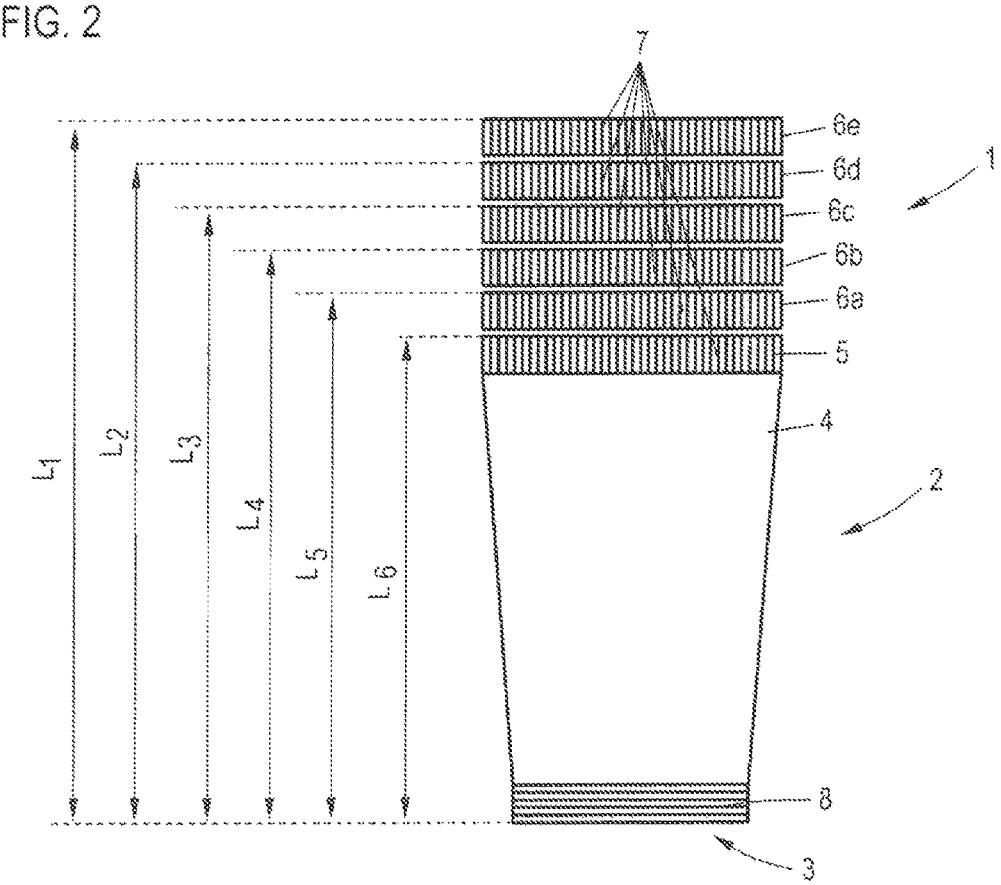
FIG. 2 is a schematic diagram of a second embodiment of a knitted-fabric part including a basic part and five extension parts.

As only one extension part 6 is provided, the knitted-fabric part 1 of FIG. 1 can only be shortened, starting from the initial measure $L_1$, to a shortened measure $L_2$. FIG. 2 shows an embodiment of a knitted-fabric part 1 with a greater scope concerning the length variation. The knitted-fabric part 1 comprises a basic part 2, in which, however, the lower end 3 of the likewise cylindrical basic part 2 for example is open and is terminated through a cuff which is knitted here as a left/left terminal edge 8. Such a left/left terminal edge 8 is slightly thinner than a usual right/right cuff. It likewise prevents a curling, but also offers the possibility, compared to the basic part portion 4 which mostly is slightly thicker and forms the essential part of the basic part 2, to apply an adhesive coating made of silicone, at the inner side of the terminal edge 8, to obtain a good hold of the basic part, which is configured as a leg sock 1 on the skin of the wearer.

The region of the basic part portion 4 is adjoined by a cuff 5, which forms the terminal end of the basic part 2.

In this example, the cuff 5 is followed by a first extension part 6a which again is connected separably, i.e. detachably, with the basic part 2 through an unravelable connecting thread, not shown in detail. This first extension part 6a is adjoined by a second extension part 6b which is assumed to correspond to the first extension part 6a regarding knitting type and length. The second extension part 6b is also connected through a discrete connecting thread with the first extension part 6a, i.e. it can also be separated or detached.

The second extension part 6b is followed by a third extension part 6c which is connected through a discrete connecting thread with the second extension part 6b, i.e. it can also be individually separated therefrom. This third extension part 6c is followed by a fourth extension part 6d that is also connected through a separable connecting thread with the third extension part 6c. The upper terminal end is finally formed by a fifth extension part 6e which is also connected through a discrete unravelable connecting thread with the fourth extension part 6d. For example, all the extension parts 6a-6e are knitted in the same way, in the shown example respectively as a cuff 7, as indicated by the hatching in FIG. 2. They may all have the same length, corresponding to the length of the cuff 5, but it is not necessarily a requirement.

All five extension parts 6a-6e have the same diameter, and they continue the basic part 2 quasi-cylindrical. As they all are interconnected respectively through a discrete, unravelable connecting thread, there are many length variation possibilities, as shown in FIG. 2. Starting out from of a total length $L_1$ of the knitted-fabric part 1, the knitted-fabric part 1 can be shortened to, altogether, five other defined lengths.

If the connecting thread between the fifth extension part 6e and the fourth extension part 6d is unravelled and drawn out, the fifth extension part 6e is removed, so the knitted-fabric part 1 can be shortened to the length $L_2$.

If, however, the connecting thread, which connects the fourth extension part 6d with the third extension part 6c is cut open and unravelled or drawn out, the knitted-fabric part 1, can be shortened, starting from the length $L_1$, to the length $L_3$, as a result then the extension parts 6e and 6d are separated.

A shortening to the length $L_4$ is possible by the connecting thread connecting the third extension part 6c with the second extension part 6b being unravelled and drawn out. The extension parts 6e, 6d and 6c are separated.

If the connecting thread connecting the second extension part 6b with the first extension part 6a, is unravelled, a shortening to the length $L_5$ is possible, by unravelling this connecting thread the extension parts 6e, 6d, 6c and 6b are jointly removed.

If, finally, the connecting thread connecting the first extension part 6a with the basic part 2 or the cuff 5 thereof is unravelled, the maximum shortening to the length $L_6$ is possible, all the connecting knitted-fabric parts 6e-6a are removed. The user has many length variation possibilities with such a knitted-fabric part 1.

While the FIGS. 1 and 2 only show one extension part (FIG. 1) or five extension parts (FIG. 2), it is possible to provide two, three or four extension parts or also more than five extension parts.

In the embodiment according to FIG. 2, it is assumed that all five extension parts 6a-6e are knitted as a cuff 7, i.e. in right/right structure or 1:1 structure. This now leads to the fact that after a shortening of the knitted-fabric part 1 it is ensured that the remaining residual knitted-fabric part 1 is terminated through a cuff, namely one of the remaining extension parts 6d-6a or the cuff 5 itself. It is ensured that the remaining knitted-fabric part 1 cannot curl or unravel.

The extension parts preferably are knitted from the same knitted-fabric thread as the basic part 2, such as PA, PP, or a PES thread or a natural thread. In addition, each knitted-fabric thread respectively used can have the same color in every part, so the knitted-fabric part 1 has a uniform color over its total length, for example, black or gray etc. It is conceivable to select a color for the extension parts different from the color of the basic part, or to select a knitted-fabric thread with different color for every extension part etc. Here, also in view of the design of the knitted-fabric part 1 there are remarkable variation possibilities. It is expedient to select the respective connecting thread in a color, which clearly differs from the one of the respectively adjacent knitted fabric, so the connecting thread can be easily found when it is to be unravelled.

Figure 3:
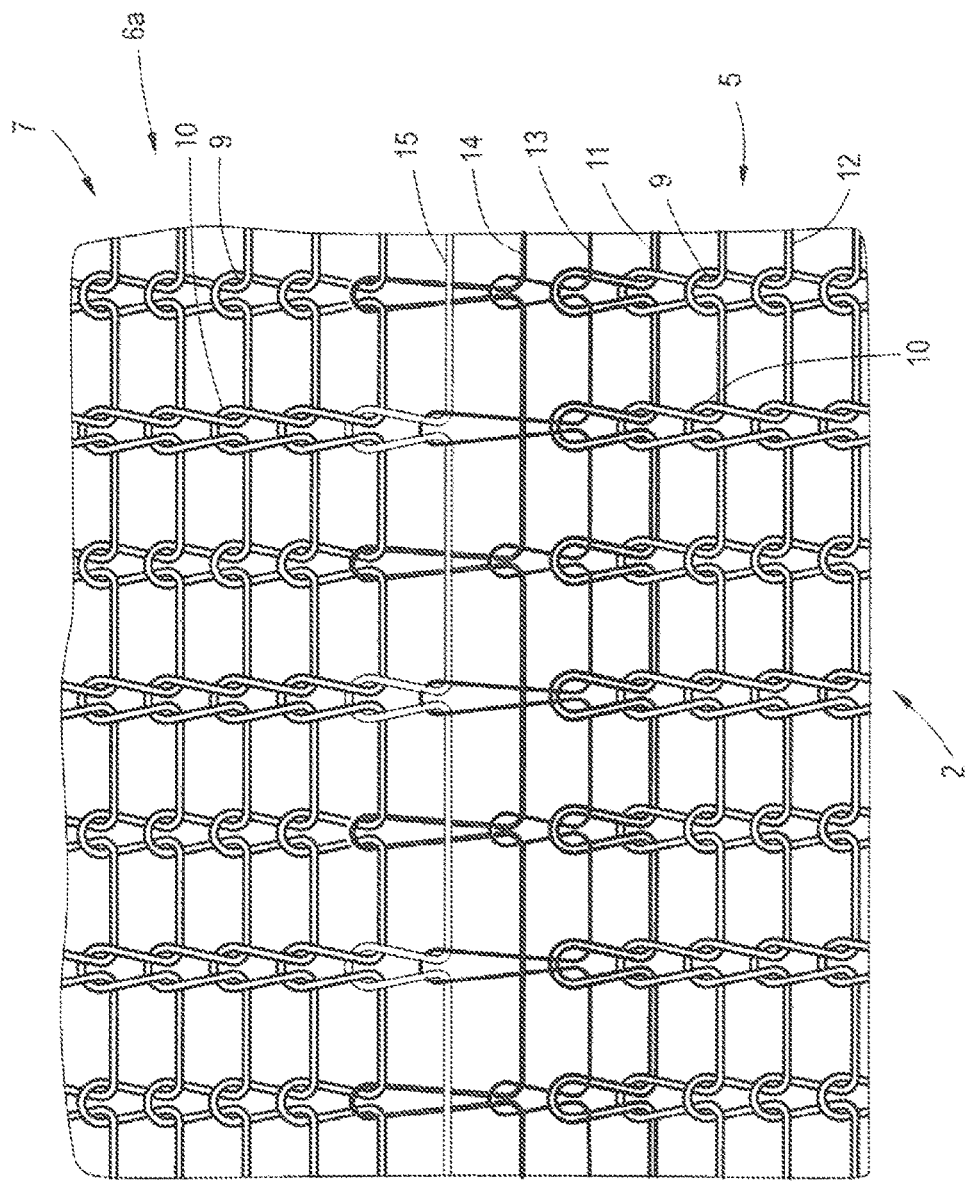
FIG. 3 is a schematic diagram of a stitch pattern as a connecting region of two parts through a connecting thread.

FIG. 3 shows for example a stitch pattern which shows the transition between a first cuff and a second cuff, and is to be read for each transition between the basic part 2 and the extension part 6 according to FIG. 1 or between the basic part 2 and the extension part 6a and any further transition from one extension part to the next extension part.

It is to be assumed that the cuff 5 of the basic part 2 is shown in the lower region, while a detail of the cuff 7 of the first extension part 6a is shown in the upper region.

As shown by this schematic diagram of the stitch pattern of FIG. 3, the cuff 5 is knitted in right/right structure or 1:1 structure with firm edge. Along the individual stitch wales, in the respective stitch wale only right stitches 9 or only left stitches 10 are knitted.

To the last stitch course of the cuff 5 there is then knitted the unravelable connecting thread 11, which preferably has a different color than the knitted-fabric thread 12 from which the cuff 5 is knitted.

To the connecting thread 11 there is then knitted the cuff 7 likewise with firm edge, beginning with a net course 13, whereby the thread forming the net course 13 forms right and left stitches, depending on the stitch wale into which it is knitted. After the net course 13 there is then knitted a first right/left course 14 in the back and a second right/left course 15 in the front. These two right/left courses 14, 15 are adjoined by the further cuff 7 with its stitch courses, again knitted in right/right structure or 1:1 structure that again only right or only left stitches are knitted in the respective stitch wale. Although not represented, each cuff 5 or 7 is knitted with firm edge, so that when the separating thread 11 is cut open and drawn out for detaching the connection of the two cuffs 5, 7, none of the cuffs 5 or 7 is unravelled.

If now starting out from the knitted-fabric part 1 of FIG. 2, the knitted-fabric part 1 is to be shortened and the corresponding knitted-fabric parts 6a-6e are to be separated, it is merely necessary to cut open the connecting thread 11 at one or several places and to draw it out, so the connection between the cuff 5 and the cuff 7, i.e. between the basic part 2 and the extension part 6a is separated. Here, the remaining knitted-fabric part 1 only has the length $L_6$, when starting out of the example of FIG. 2. The cuff 5 forms the terminal end.

As described, each connection among the different extension parts 6a-6e is realized in this way and each cuff of the respective extension parts 6a-6e is terminated through a respective firm edge on both sides. An arbitrary length variation may be obtained by simply unravelling the respective connecting thread and the termination of the remaining knitted-fabric part 1 through a cuff with firm edge is ensured.

For reasons of a better recognisability, the net courses 13 and the right/left courses 14, 15 and the other courses of the cuff 7 are respectively shown in different knitting threads. The cuff 5 and the cuff 7 are respectively knitted of at least one knitting thread, while the connecting thread 11 is a discrete thread, where applicable, of a color different from that of these knitted-fabric threads.

FIG. 4 shows another embodiment example of a knitted-fabric part 1 according to the disclosure including the basic part 2 and, in the shown example, of two extension parts 6a, 6b. The basic part 2 again is assumed to be open near its lower end 3 and terminated with a usual cuff 16 there. At the upper end of the basic part 2 there is knitted a cuff 5.

Unlike the above-described embodiments where each extension part 6, 6a-6e is knitted over its total length as a cuff 7, the two extension parts 6a, 6b according to FIG. 4 are knitted as a cuff 7 with firm edge respectively only near its upper and lower end. Between there is located a knitted-fabric portion 17 which is knitted in any other structure type. The cuff 5 and the cuff 7 of the first knitted-fabric part 6a are interconnected through a discrete, unravelable connecting thread 11. The upper cuff 7 of the extension part 6a is connected with the lower cuff 7 of the second extension part 6b also through a discrete, unravelable connecting thread 11. Each cuff 5, 7 is configured with a firm edge, so that upon detaching the respective connecting thread again a firm terminal end edge through a cuff 7 or 5 is ensured, which prevents a curling.

An embodiment of a knitted-fabric part 1, which is again slightly different, is shown in FIG. 5. The basic part 2 with the basic part portion 4 is assumed to be open at the lower end 3 and is terminated through a right/right cuff 16. At the upper end there is again located the right/right cuff 5.

Two extension parts 6a, 6b are provided with a cuff 7 only in the respective upper end, however, and in the remaining length region show a knitted-fabric portion 17 that again may be knitted in an arbitrary structure type.

In this configuration, the cuff 5 is connected through the connecting thread 11 with the knitted-fabric portion 17 of the extension part 6a, as the cuff 7 of the knitted-fabric part 6a is connected with the knitted-fabric portion 17 of the second extension part 6b through a discrete connecting thread 11. A connection from cuff to cuff is not compulsory, and it is sufficient when a connection between a cuff forming the upper terminal end and an arbitrary knitted-fabric portion forming the lower terminal end is realized.

If in this embodiment example one of the connecting threads is separated, the one or more extension parts will be separated here. It is preferable that the corresponding knitted-fabric part terminal end is given through a cuff, which prevents a curling, this being either a cuff 7, when only the extension part 6b is separated, or this being the cuff 5, when both extension parts 6a, 6b are separated. The corresponding cuffs are configured with firm edge so that when one of the connecting threads is drawn, an unravelling is excluded. The respective knitted-fabric portion 17 can be terminated arbitrarily; it may unravel itself after the separating, because it is no longer needed.

In the two configurations according to the FIGS. 4 and 5 only two extension parts 6a, 6b are provided for example. Arbitrary variation possibilities are given on only one extension part or over two extension parts being provided. These may continue the basic part 2 cylindrically, as described in the embodiment according to FIG. 2. With all the embodiments it is possible to continue, if provided, the conical shape of the basic part 2 conically.

As described, it is possible to use different knitted-fabric threads, which likewise applies to the embodiments of the FIGS. 4 and 5. The separating thread should have a color, which clearly distinguishes it from the knitted-fabric threads of the adjacent parts.

The knitted-fabric parts 1 in the FIGS. 1, 2 and 4, 5 are to be worn, as described, at the leg. The knitted-fabric part 1 of FIG. 1 is a stump sock, as it is closed at the lower end; it is drawn over a residual limb. The knitted-fabric parts 1 of the FIGS. 2, 4 and 5, however, are open at their lower end; they may be sleeves for volume compensation socks in connection with a liner to be drawn over a residual limb. Therefore, for example in the region of the lower end 3, i.e. in the region of the terminal edge 8 or of the cuff 16, there can be provided an adhesive layer on the inner side which comprises a stretchable elastomer or an elastomer gel comprising an elastomer and a plasticizer oil.

The features may be employed in different combinations from those shown herein. While the foregoing embodiments have been described and shown, alternatives and modifications of these embodiments, such as those suggested by others, may be made to fall within the disclosure.

The invention claimed is:

1. A knitted-fabric part, comprising:
   a basic part knitted with at least one knitted-fabric thread;
   at least one extension part attached to the basic part to form a contiguous and intact structure;
   at least one unravelable connecting thread attaching the basic part to the at least one extension part, such that removal of the at least one unravelable connecting thread separates the basic part from the at least one extension part;
   wherein the basic part is terminated at an end which faces the at least one extension part through a knitted cuff defining an anti-fray edge comprising at least a net course and a locking course;
   wherein the locking course comprises at least one left/right course.

2. The knitted-fabric part according to claim 1, wherein the at least one unravelable connecting thread is a single unravelable connecting thread interconnecting the basic part and the at least one extension part.

3. The knitted-fabric part according to claim 1, wherein the at least one extension part includes at least two separable extension parts extending in a longitudinal direction relative to the basic part, the first and second extension parts are respectively interconnected by one of the at least one unravelable connecting thread.

4. The knitted-fabric part according to claim 2, wherein the first extension part and the second extension part are knitted as a cuff with anti-fray edges comprising a net course and a locking course, the locking course comprising at least one left/right course on both sides.

5. The knitted-fabric part according to claim 2, wherein the first extension part and the second extension part each have a cuff with an anti-fray edge on a respective side which faces away from the extension part which respectively lies closer to the basic part.

6. The knitted-fabric part according to claim 1, wherein the at least one connecting thread is knitted right/left, right/right, or in tubular structure.

7. The knitted-fabric part according to claim 1, wherein the at least one connecting thread has a color different from threads forming the basic part.

8. The knitted-fabric part according to claim 1, wherein the at least one extension part defines opposed open ends.

9. The knitted-fabric part according to claim 1, wherein the basic part has a closed end and an open end, the open end being adjacent to the at least one extension part.

10. The knitted-fabric part according to claim 1, wherein the basic part is generally tubular and forms opposed first and second open ends, the basic part having a cuff at the first end.

11. The knitted-fabric part according to claim 1, wherein the basic part and the at least one extension part are generally tubular.

12. The knitted-fabric part according to claim 11, wherein the basic part has a conical shape.

13. The knitted-fabric part according to claim 1, wherein the basic part and the at least one extension part are formed from a flat knitted-fabric or a circular knitted-fabric.

14. The knitted-fabric part according to claim 1, wherein the basic part has an adhesive layer located about at least a portion of an inner side of a first open end thereof.

15. The knitted-fabric part according to claim 14, wherein the adhesive layer is selected from the group consisting of a stretchable elastomer, an elastomer gel, and a plasticizer oil.

16. A knitted-fabric part, comprising:
   a basic part knitted with at least one knitted-fabric thread and tubular in shape;
   a first extension part having a first end attached to the basic part to form a contiguous and intact structure, the first extension part being knitted with at least one knitted-fabric thread and is tubular in shape;
   a first unravelable connecting thread attaching the basic part to the first extension part, such that removal of the first unravelable connecting thread separates the basic part from the first extension part;
   a second extension part having a first end attached to a second end of the first extension part to form a contiguous and intact structure therewith;
   a second unravelable connecting thread attaching the second extension part to the first extension part, such that removal of the second unravelable connecting thread separates the second extension part from the first extension part;
   wherein the basic part terminates at an end facing the first extension part and comprising a knitted cuff defining an anti-fray end comprising a net course and a locking course, the locking course comprising at least one left/right course.

17. The knitted-fabric part according to claim 1, wherein the first and second extension parts each define opposed open ends.

18. The knitted-fabric part according to claim 1, wherein the first and second extension parts are each knitted as a cuff with anti-fray edges on both sides.

19. A knitted-fabric part, comprising:
   a basic part knitted with at least one knitted-fabric thread;

at least one extension part attached to the basic part to form a contiguous and intact structure;

at least one unravelable connecting thread attaching the basic part to the at least one extension part, such that removal of the at least one unravelable connecting thread separates the basic part from the at least one extension part;

wherein the basic part is terminated at an end which faces the at least one extension part through a knitted cuff defining an anti-fray edge;

wherein the at least one extension part is knitted as a cuff with anti-fray edges on both sides;

wherein the basic part and the at least one extension part are formed from a flat knitted-fabric or a circular knitted-fabric;

wherein each of the anti-fray edges comprises at least a net course and a locking course, the locking course comprising at least one left/right course.

20. The knitted-fabric part of claim 1, wherein the locking course comprises at least a second left/right course arranged to alternate with the first left/right course.

\* \* \* \* \*